US005698207A

United States Patent [19]

Staats

[11] Patent Number: 5,698,207

[45] Date of Patent: *Dec. 16, 1997

[54] BURN TREATMENT COMPOSITION

[75] Inventor: Victor J. Staats, Miami Beach, Fla.

[73] Assignee: International Laboratory Technology Corp., Miami Beach, Fla.

[*] Notice: The term of this patent shall not extend beyond the expiration date of Pat. No. 5,417,968.

[21] Appl. No.: 507,763

[22] Filed: Jul. 26, 1995

[51] Int. Cl.$^6$ .................... A61K 31/74; A61K 31/785; A01J 21/00

[52] U.S. Cl. ...................... 424/78.06; 424/78.07; 424/405; 424/409; 424/411; 514/887; 514/928

[58] Field of Search .............. 424/78.06, 78.07, 424/405, 409, 411; 514/887, 928

[56] References Cited

U.S. PATENT DOCUMENTS 5,232,691  8/1993  Lemole .................... 424/78.02
5,417,968  5/1995  Staats ..................... 424/78.07

*Primary Examiner*—Keith MacMillan
*Attorney, Agent, or Firm*—Robert M. Downey, P.A.

[57] ABSTRACT

An antimicrobial composition for application to exposed wounds such as burns and ulcers includes a quaternary ammonium compound blend, a stabilizer, a nonylphenol polyethylene glycol ether, a hydrophilic polymer, sodium lithium magnesium silicate, a hydrophobic waterproofing agent, aluminum sulfate, triethanolamine and water.

7 Claims, No Drawings

BURN TREATMENT COMPOSITION

BACKGROUND OF THE INVENTION

1. Field of the Invention

The present invention relates to a protective composition for application to open wounds, and more particularly to a antiviral, antibacterial, antifungal barrier composition for topical application in order to coat and protect acute and/or chronic wounds or ulcerations wherein raw tissue is exposed.

2. Description of the Related Art

When skin is injured by any trauma which may cause an acute wound, such as a burn or scrape, or by chronic wounds such as a stasis ulcer, the normal protective skin barrier is compromised, subjecting the wound to potentially severe infection. In some instances, particularly with severe burn cases, an infection can be fatal. Open wounds which expose raw tissue generally require intensive care, including irrigations to hydrate the wound and dressings which protect the tissue from exposure to infection. However, the practice of irrigating and applying dressings to wounds results in the trapping of moisture, with the dressing acting as an incubator for fungus, bacteria and viruses. Accordingly, while it is imperative to irrigate and dress open wounds, the danger of infection is always a concern.

In view of the foregoing, it would be beneficial to introduce a waterbased, longlasting, non-toxic, antifungal, antibacterial, antiviral substance to open wounds, with or without a dressing.

SUMMARY OF THE INVENTION

The present invention is directed to an antimicrobial composition for protecting open wounds such as burns, scrapes, and ulcers. Specifically, the present invention provides a novel composition which is adapted for use in the form of a cream, lotion or gel for topical application to an open wound in order to cover and protect the wound, providing an antiviral, antibacterial, and antifungal protective barrier. The active antimicrobial component of the composition consists of a mixture of a quaternary ammonium compound and a nonylphenol polyethylene glycol ether.

In accordance with the foregoing, it is a primary object of the present invention to provide an antiviral, antibacterial, antifungal barrier composition for topical application to open wounds of the skin including burns, scrapes, and ulcers.

It is a further object of the present invention to provide antiviral, antibacterial, and antifungal composition for coating acute or chronic wounds or ulcerations where raw tissue is exposed in order to protect the wound from exposure to fungus, bacteria, and viruses.

It is still a further object of the present invention to provide an antiviral, antibacterial, antifungal composition for topical application to open wounds such as burns, scrapes and ulcers for use in combination with or without a dressing in order to protect the wound from exposure to fungus, bacteria and virus.

It is yet a further object of the present invention to provide an antiviral, antibacterial, and antifungal composition as set forth above which is waterbased, non-occlusive, longlasting, and non-toxic.

It is still a further object of the present invention to provide a composition as set forth above which is analgesic and which further has excellent moisturizing characteristics.

In accordance with these stated objects and advantages and other inherent objects and advantages of the present invention, the composition is more fully described in the following detailed description and the scope of the invention is indicated in the claims.

DETAILED DESCRIPTION OF THE PREFERRED EMBODIMENT

The present invention is directed to an antimicrobial composition for topical application to acute and/or chronic wounds or ulcerations wherein raw tissue is exposed in order to provide an antiviral, antibacterial, and antifungal protective barrier. In use, the composition, in the form of a creme or gel, is topically applied to an open wound by spreading the composition over the entire exposed area of the wound and skin surrounding the periphery of the wound. The composition should be spread to apply a coat of uniform thickness completely covering the wound. Thereafter, dressing may be applied if needed. While the composition is longlasting, the dressing should be changed regularly, applying the composition as needed in order to maintain a protective coating.

The composition includes a functional substance which is biologically active against a broad spectrum of viruses, bacteria, fungi, and other pathogenic species. In a preferred embodiment, the preferred biologically active substance is a quaternary ammonium compound, preferably BTC 2125M, manufactured by Stepan, and shown by the general formula:

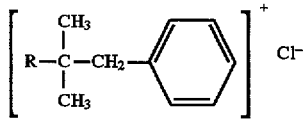

R is 60% C14, 30% C16, 5% C12, 5% C18 n-alkyl dimethyl benzyl ammonium chloride

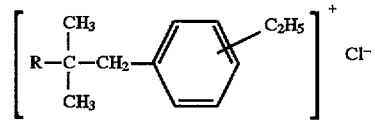

R is 68% C12, 32% C14 n-alkyl dimethyl ethylbenzyl ammonium chloride

The quaternary ammonium compound is preferable present in an amount of between 0.00005%–0.00025% (50 ppm–250 ppm) by weight of the composition. In the preferred embodiment, the quaternary ammonium compound may be used alone or in combination with a nonionic surfactant such as Tergitol NP-9 (Nonoxynol 9) or Triton X-100. Other nonionic surfactants known in the art may further be effective in combination with the quaternary ammonium compound to achieve an effective kill of virus, bacteria, and fungi. The use of a nonionic surfactant, such as Nonoxynol 9, in combination with the quaternary ammonium compound provides a synergistic effect, producing an increased activity against pathogenic species such as virus, bacteria, and fungi. Further, Tergitol Nonoxynol 9 serves as a highly effective wetting agent for application of the composition to a skin surface or substrate, effectively broadening the effectiveness of the quaternary ammonium compound throughout the entire exposed area of the wound. The nonionic surfactant further serves as a spreading agent, enabling the composition to be spread evenly over the entire applied surface, thus achieving and maintaining a uniform microbicidal effectiveness throughout the applied area. The nonionic surfactant is preferably present in the amount of between 0.2%–8% by weight of the composition.

The composition further includes 1,3 butylene glycol as a stabilizer, and is present in the amount of between 0.5%–7% by weight of the composition. 1,3 butylene glycol not only effectively stabilizes the composition, but further aides in dispersion. The composition further contains a hydrophobic, waterproofing agent. In a preferred embodiment, GANEX V-220, manufactured by GAF Chemicals Corporation, provides an ideal waterproofing agent. GANEX V-220 is a polymer derived from vinylpyrrolidone and a long chain alpha olefin represented by the general formula:

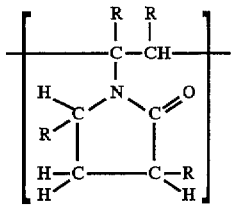

wherein R is alkyl or hydrogen.

In the preferred embodiment, the hydrophobic, waterproofing agent is a PVP/eicosene copolymer (polyvinylpyrrolidone and eicosene) and is present in the amount of between 0.5%–6% by weight of the composition.

The vehicle for the composition consists of 0.01%–10% by weight of a resinous hydrophilic water-swellable polymer that provides thickening and promotes retention of water in the composition. This is particularly important when protecting a burn wound in order to promote irrigation. Many such resins are contemplated within the scope of the present invention. In a preferred embodiment, a cross-linked acrylic acid polymer, such as Carbopol 940, manufactured by B.F. Goodrich, is an ideal vehicle for the composition.

The composition may further be provided with an inorganic silicate, such as sodium lithium magnesium silicate in an amount of between 0.01%–7% by weight of the composition. The inorganic silicate helps prevent the composition from being washed away by bodily fluids which are generally high in salt content. The inorganic silicate further provides a shear, sensitive structure to the composition, making the composition compatible with open wounds.

Aluminum sulfate $AL_2(SO_4)_3$, may be added to the composition in an amount of between 0.025%–10% by weight for purposes of providing an enhanced antifungal effectiveness.

Triethanolamine, provided in an amount of between 0.06%–2% by weight, is effective as a catalyst to gel the composition. Titanium dioxide may further be provided in an amount of between 0.5%–6% by weight to help smooth out the composition and provide a desirable texture. The remainder of the composition consists of water.

The formation of the composition includes the use of three separate mixing tanks. In a first stainless steel mixing tank, approximately ⅓ of the total volume of water is mixed with the hydrophilic copolymer and sodium lithium magnesium silicate. The contents in the first mixing tank are mixed at high speed shear for 30 minutes or until fully blended.

In a second stainless steel mixing tank, ⅓ of the total volume of water is combined with the quaternary ammonium compound (BTC 2125M), Tergitol, and Aluminum Sulfate. The combined contents are stirred at a slow speed until the Aluminum Sulfate is completed dispersed within the mixture.

In a third mixing tank, the remaining volume of water is combined with 1,3 butylene glycol and GANEX V-220, mixing at a slow speed, while bringing the temperature of the third mixture to 140° Fahrenheit. The third mixture is maintained at this temperature for approximately 15 minutes.

Next, the mixture in the first mixing tank (first mixture) is heated to approximately 120° Fahrenheit. Thereafter, the third mixture and first mixture are combined at a high speed sweep mix, mixing for 10 minutes. One-fourth of the total amount of Triethanolamine is then added, mixing for approximately 10 minutes.

Next, the second mixture, in the second stainless steel mixing tank, is very slowly added to the combined first and third mixture, mixing at a high speed sweep mix while adding the remaining ¾ of Triethanolamine. The combined mixture is allowed to cool while adding Titanium Dioxide with a sweep mix until a homogenous thick mixture is achieved.

While the composition of the present invention has been described in what is considered to be a preferred and practical embodiment, it is recognized that departures may be made within the spirit and scope of the invention which is not to be limited except as set forth in the following claims and within the Doctrine of Equivalents.

Now that the invention has been described,
What is claimed is:

1. A composition for topical application to open wounds comprising:

a quaternary ammonium compound in an amount of between 0.00005% to 0.00025% by weight of said composition, a stabilizer in the amount of between 0.5%–7.0% by weight of said composition, a nonylphenol polyethylene glycol ether in an amount of between 0.02%–8.0% by weight of said composition, a hydrophilic film forming compound in an amount of between 0.01%–10.0% by weight of said composition, a hydrophobic waterproof polymeric compound in an amount of between 0.5%–10.0% by weight of said composition, triethanolamine in an amount of between 0.06%–2.0% by weight of said composition, and water.

2. The composition as set forth in claim 1 further including aluminum sulfate in an amount of between 0.025%–10.0% by weight of said composition.

3. The composition as set forth in claim 1 further including titanium dioxide in an amount of between 0.5%–6.0% by weight of said composition.

4. The composition as set forth in claim 1 wherein said quaternary ammonium compound is a blend of n-alkyl dimethyl benzyl ammonium chloride and n-alkyl dimethyl ethylbenzyl ammonium chloride.

5. The composition as set forth in claim 4 wherein said hydrophobic waterproof polymeric compound is a copolymer of polyvinylpyrrolidone and eicosene.

6. The composition as set forth in claim 5 wherein said hydrophilic film forming compound is a cross-linked acrylic acid polymer.

7. A composition for topical application to open wounds comprising:

a biocidally effective amount of a functional substance, a hydrophilic water-swellable polymer including a cross-linked acrylic acid polymer and an inorganic silicate providing a skin compatible polymeric vehicle, a hydrophobic waterproof polymeric compound in the form of a copolymer of polyvinylpyrrolidone and eicosene, triethanolamine, a stabilizer, titanium dioxide, and water.

* * * * *